United States Patent [19]

Moore et al.

[11] Patent Number: 4,755,744

[45] Date of Patent: Jul. 5, 1988

[54] PLATED SENSOR FOR MONITORING CORROSION OR ELECTROPLATING

[75] Inventors: Clifford G. Moore, Arcadia, Calif.; Herbert P. Silverman, Seattle, Wash.; James R. Bredow, La Habra, Calif.

[73] Assignee: Rohrback Corporation, Seattle, Wash.

[21] Appl. No.: 21,013

[22] Filed: Jan. 21, 1986

[51] Int. Cl.⁴ .......................................... G01R 27/02
[52] U.S. Cl. .............................. 324/65 CR; 324/71.2; 204/404
[58] Field of Search ............... 324/65 CR, 65 P, 71.2; 73/86; 338/13; 427/8-10; 204/1 T, 14.1, 404

[56] References Cited

U.S. PATENT DOCUMENTS

| | | | |
|---|---|---|---|
| 2,851,570 | 9/1958 | Schaschl | 201/63 |
| 2,864,925 | 12/1958 | Ellison | 201/63 |
| 2,978,364 | 4/1961 | Blaustein | 117/227 |
| 3,153,217 | 10/1964 | Cramer et al. | 324/65 CR |
| 3,197,724 | 7/1965 | Marsh | 324/65 CR |
| 3,669,868 | 6/1972 | Lieber et al. | 204/228 |
| 4,331,699 | 5/1982 | Suzuki et al. | 427/8 |
| 4,331,702 | 5/1982 | Hieber et al. | 427/10 |
| 4,338,563 | 7/1982 | Rhoades et al. | 324/65 |
| 4,350,717 | 9/1982 | Araki et al. | 427/8 |
| 4,477,484 | 10/1984 | Paoletti et al. | 427/10 |
| 4,479,980 | 10/1984 | Acosta et al. | 427/10 |
| 4,514,681 | 4/1985 | Finley et al. | 324/65 |

Primary Examiner—Reinhard J. Eisenzopf
Assistant Examiner—Jack B. Harvey
Attorney, Agent, or Firm—Gausewitz, Carr & Rothenberg

[57] ABSTRACT

A high sensitivity electroplating or corrosion sensor and method for sensing employing a relatively strong, self-supporting electrically conductive substrate of high resistivity and a test coating that is electroplated directly onto the substrate. For corrosion monitoring, a test element of the sensor is formed of a thick, high resistivity substrate, such as stainless steel, upon which is electroplated a thin test coating of material to be tested in a corrosive environment. For many applications, the ratio of resistivity of the substrate to resistivity of the test coating is substantially equal to the ratio thickness of the substrate to thickness of the test coating, which ratios may be about 40 to 1. The sensor may be employed in the monitoring of electroplating by immersing the stainless steel substrate in the electrolytic bath with the object to be plated and measuring the decreasing parallel resistance of the substrate and coating that is plated upon the substrate during a plating of the object. To decrease resistance measuring noise due to currents generated in the plating or corrosion sensor by external currents, the power supply is connected to the sensor substrate to cause equal and opposite current components to flow in the substrate.

32 Claims, 3 Drawing Sheets

PLATED SENSOR FOR MONITORING CORROSION OR ELECTROPLATING

BACKGROUND OF THE INVENTION

The present invention relates to electrical resistance corrosion and plating sensors, and more particularly concerns sensors that are of increased sensitivity for monitoring corrosive tendencies or plating processes.

A common method of continuous measurement of corrosion characteristics employs resistance measurement of a metallic, corrodible or erodible test element to indicate, by change of resistance, the amount of metal that has been lost by corrosion or erosion over a period of time. A widely used sensor for this measurement is known under the trademark Corrosometer manufactured by Rohrback Corporation, assignee of this application. One such sensor employs a tubular metallic test element loop or wire, part of which operates as a reference element made of the same material as the test element. The reference element is protected from the environment while the test element is exposed to the environment. Alternating current is passed through the elements and electrical resistance of each is measured while or after the sensor has been immersed in an environment of which corrosive tendencies are to be monitored. Because resistance varies with the amount of metal in the test element, measurement of test element resistance provides an indication of metal loss and, therefore, of corrosion. However, because resistance of the metal also changes with temperature, a reference element is provided, made of the same material as the test element, and having the same temperature resistance characteristics. Thus, changes in resistance of the test element that are due to long term, relatively slow temperature variation may be eliminated by comparison of resistances of the test and reference elements. Other sensors may include a cylindrical metallic test element carrying an inner reference element made of the same material as the test element with the interior of the test element filled with a thermally conductive, electrically nonconductive compound, thereby providing physical support for the preferably very thin wall of the test element.

A major shortcoming of presently available electrical resistance corrosion sensors is lack of desired sensitivity to low corrosion rates (in the order of less than about 2 mils per year) due to physical constraints imposed by pressures and flow conditions in a process environment that is being monitored. For structural reasons the wall thickness of tubular loop test elements or straight cylindrical test elements is usually required to be 4 mils or greater. Similarly, the diameter of a wire loop must be at least 20 mils for adequate physical structure and strength necessary to withstand the process pressures and flow conditions.

Sensitivity of a corrosion sensor is directly related to its initial resistance and, therefore, to the initial thickness of the test material. Sensitivity is inversely related to the test material thickness. To provide increased sensitivity of such corrosion sensors it has been suggested to employ a relatively thin coating on a relatively thick ceramic or other substrate that is not electrically conductive. However, there are significant problems involved in the accurate coating of different ones of the desired test materials upon the nonconductive substrate. Such manufacturing problems and costs have heretofore made such probes practically unfeasible. Thus, corrosion sensors of the prior art are of a limited sensitivity.

In the electroplating of various objects, monitoring of the plating process has been carried out by periodically removing a test coupon from the bath and measuring its plating thickness. Precision measurement of plating thickness as the electroplating process proceeds has not been available. Electrical resistance measurements, for example, those made by measuring the continually decreasing resistance of a plated test coupon during the progress of an electrolytic plating process, have not been possible. The electrical current flowing in the plating tank causes sufficient interference to the measuring circuitry that measurement of resistance is impossible. Moreover, such sensors, when used for monitoring corrosive tendencies of a fluid environment, are generally not renewable and must be discarded after a finite period of use. These sensors are relatively expensive, at least in part due to manufacturing procedures which are necessarily intricate and highly precise, and therefore, renewability is desirable.

Accordingly, it is an object of the present invention to enable sensing of plating processes or corrosive tendencies in a manner which eliminates or minimizes above-mentioned problems.

SUMMARY OF THE INVENTION

In carrying out principles of the present invention, in accordance with a preferred embodiment thereof, a corrosion or electroplating sensor, having a test element adapted to be exposed to an environment to be monitored and a reference element protected from such environment, is connected to an instrument for comparing the electrical resistance of the elements for determination of test element thickness. The test element comprises a substrate formed of electrically conductive material, having an electrically conductive test coating thereon, the test coating having an electrical resistivity that is considerably less than the electrical resistivity of the substrate. This relation of resistivities enables the test coating to be much thinner than the substrate, which accordingly can have a substantial strength and be self-supporting, and enables the test coating to be electroplated directly upon the conductive substrate.

In application of the sensor for monitoring of electroplating, the test element substrate is connected to the plating power source so as to cancel a major portion of measurement noise currents. The plating process causes the substrate to be plated, thereby indicating plating thickness by measurement of sensor resistance. According to another feature of the invention, and particularly for corrosion measurement, the ratio of temperature coefficients of resistance of the substrate and coating is in the range of about 0.8 to 1.2, these temperature coefficients optimumly being mutually equal. According to another feature of the invention, the ratio of substrate resistivity to test material resistivity is in the range of about 7 to 46.

DETAILED DESCRIPTION

Corrosion/Erosion Sensing

Figures 1, 6, 7:
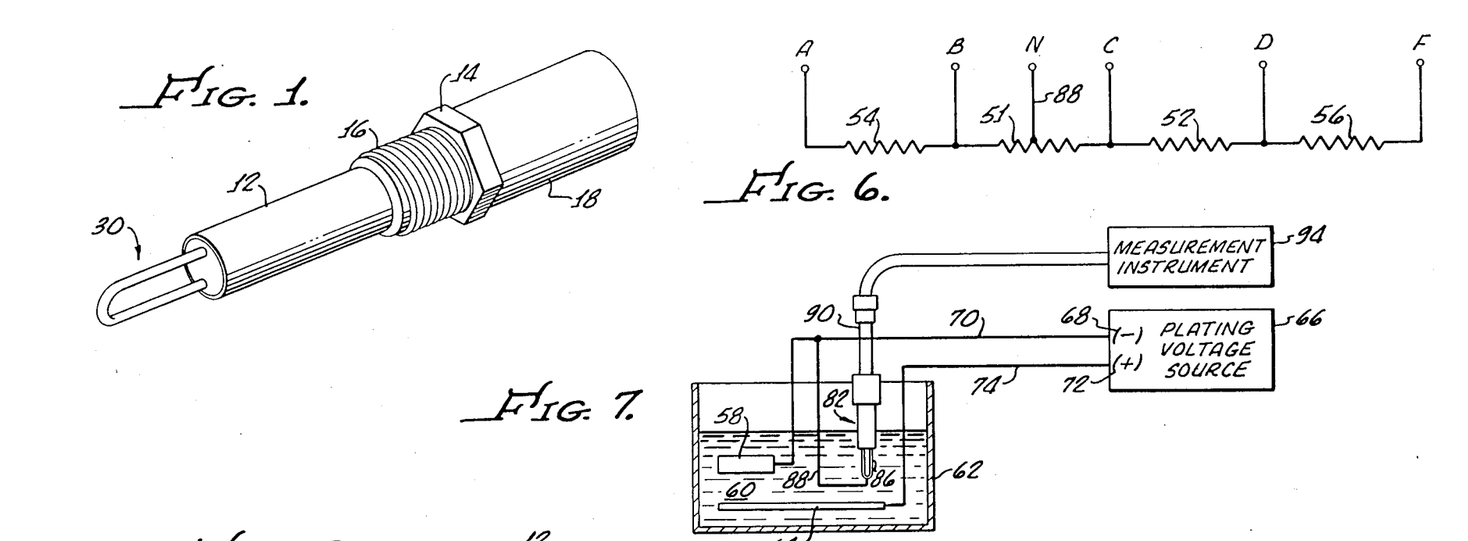
FIG. 1 is a pictorial illustration of a corrosion sensor that may be employed in the practice of the present invention.
FIG. 6 is a simplified electrical schematic diagram of portions of the sensor resistive elements having a center tap for use in monitoring of electroplating.
FIG. 7 illustrates an electrolytic plating bath in which a sensor embodying the circuit of FIG. 6 is employed.

As shown in FIG. 1, an exemplary tubular loop type corrosion sensor of a type known as a Corrosometer probe manufactured by Rohrback Corporation is shown to include a tubular test element 30 mounted in a probe body 12 which is formed with a fitting 14 adapted to receive a suitable tool for rotating the probe body to cause a threaded neck 16 on the probe body to be turned into a threaded opening (not shown) of the wall of a pipe or the like (not shown) into which the sensor will extend to expose the tubular test element 30 to the environment to be monitored. The body has a connector section 18 which includes one part of a detachable connector plug having electrical terminals connected to various points on the test and reference elements as will be described below.

Figure 2:
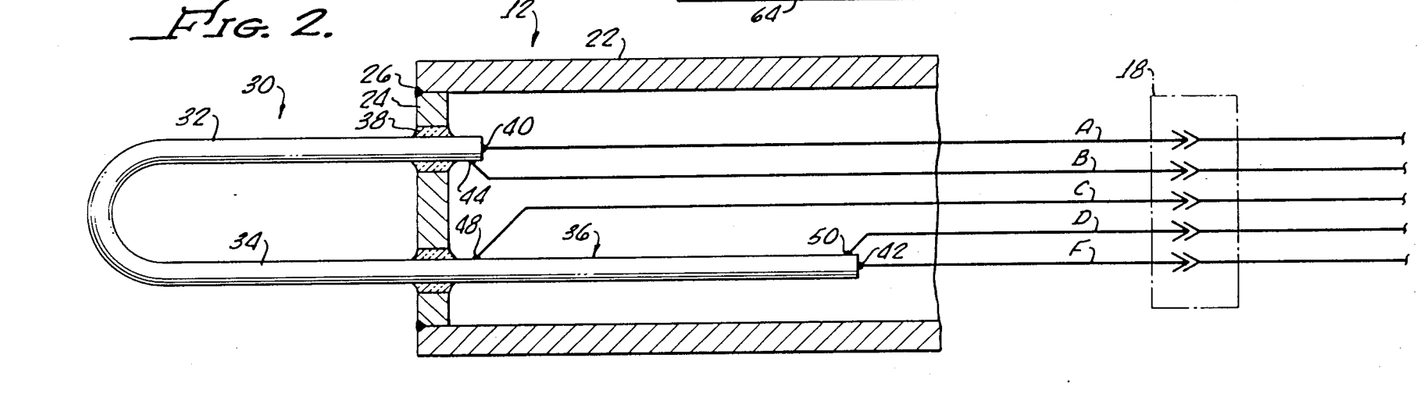
FIG. 2 is a section of a portion of the tip of the sensor of FIG. 1.

FIG. 2 shows an enlarged, fragamentary sectional view of the end of the tubular loop sensor of FIG. 1. Probe body 12 is shown as being formed of a tubular cylinder 22 having an end closed by a metalic header disk 24 which is welded at its periphery 26 to the cylinder 22. A combined test and reference element includes a substantially U-shaped portion having parallel legs 32, 34, with leg 34 extending integrally through the header 24 to form a reference element 36. Header disk 24 is formed with a pair of apertures for reception of the test element legs 32, 34. The apertures are considerably larger than the diameter of the test element tubes and the space between the walls of the header disk apertures and the tubes which extend therethrough is filled with a fused glass or other sealing material 38 which both electrically insulates the test and reference elements and hermetically seals the interior of cylinder 22.

In the illustrated embodiment, the test and reference elements are formed from a single unitary length of thin wall tubing which includes a high resistivity electrically conductive substrate and test and reference coatings electroplated directly thereon as will be more particularly described below.

For use in measurement of resistance of the sensor, terminals A and F, which are mounted within the connector portion 18, are connected by insulated electrical leads to points 40, and 42 respectively on the respective ends of the integral tubular element. Terminal B is also connected to one end of the tubular test element at a point 44 adjacent point 40. Terminal C is connected at point 48 adjacent the header disk to an end of the reference element and to one end of the test element. Terminal D is connected to the end of the reference element at point 50, adjacent point 42. Leads A and F are connected to a source of alternating current (not shown) providing a relatively small energizing current flowing through both test and reference elements. The measurement of resistance of the test element 32, 34 is made between points 44 and 48, terminals B and C, and measurement of the resistance of the reference element is made between points 48 and 50, between terminals C and D. The measurement of corrosion involves calculation of the ratio of resistance of the test element to measured resistance of the reference element. The latter is protected from the environment whereas the test element is exposed to the environment. As the test element corrodes, its thickness decreases and its resistance increases, whereas the protected reference element maintains a fixed resistance except for temperature fluctuations. As well known, both resistance measurements are subject to fluctuation with varying temperature. Preferably, the reference and test elements have the same temperature coefficient of resistance (as by making the two elements integral or of the same material) and experience the same variation in resistance with temperature changes. Therefore, that portion of the measured variation in resistance of the test element which is due to variation in temperature is eliminated from the meaurement by use of the ratio of test element resistance to reference element resistance.

Corrosion monitoring probes presently in use, with configurations exemplified by the illustrations of FIGS. 1 and 2, have employed various types of sensing elements. For example, the elements of sensor 30 of FIGS. 1 and 2 may take the form of a loop of thin wall tubing formed of a metal which is preferably the same material as the walls of the pipe or container in which corrosion is to be monitored. Wall thickness of such thin-walled tubing is usually 4 mils or greater, for structural integrity. Alternate configurations of such sensors include loops of solid wire, loops of flat metal strip or straight-walled, hollow cylinders having a relatively thin (4 mils or more) sensitive metal disk closing the end of the cylinder. These are configurations well known in the art and are shown, for example in U.S. Pat. Nos. 4,338,563 and 4,514,681. The loops or cylinder are exposed to the corrosive environment and may include an integral reference element such as reference element 36 of FIG. 2 mounted within the probe body and protected from the environment as previously described.

A major shortcoming of such probes is the relative lack of sensitivity to low corrosion rates, in the order of less than 2 mils per year (MPY). Because of flow rates, pressures and temperatures to which the test elements are exposed, they must have substantial physical structure and accordingly, in the past, have been required to be in the order of 4 mils or more in thickness. Application of a thin coating of sensing metal to a thicker, more structurally self-supporting dielectric substate is difficult and exceedingly costly. Various types of available methods for applying thin coats to nonconductive substrates are more difficult to accomplish and may provide measurement instruments which are unsatisfactory in many respects. Such methods as vapor deposition, spraying and electroless plating are not satisfactory and have not been used in the industry.

In accordance with certain features of the present invention, the sensing element of the sensor is made of a thin layer of the sensing metal of interest that is deposited by electroplating directly upon a substrate that is made of metal or other electrically conductive material. As an example, a sensor of the general configuration described above may be formed of a thin layer of copper that is deposited by electroplating directly upon a 316 stainless steel loop of tubing having a wall thickness of 4 mils. The choice of material for substrate and plating is important from the standpoint of relative resistivities. If the plated coating is to be very thin, as is required for high sensitivity measurement, and if the substrate must be relatively thick in order to provide the physical support for the electroplated coating, it is necessary that the resistivity of the substrate be significantly greater than the resistivity of the plating. Thus, the combination of copper deposited by electroplating on 316 stainless steel is feasible because the intrinsic resistivity of 316 stainless steel, which is about 74 microhm-centimeters, is approximately 43 times the intrinsic resistivity of copper, which is about 1.73 microhm-centimeters. With these materials and relative resistivities, the plated copper coating may be about 0.1 mil in thickness on a 4 mil thick stainless steel substrate. In other words, a range or relation of resistivities is chosen to give a desired range of relative thickness of plating and substrate. In the example initially given here, the ratio of resistivity of substrate to the resistivity of plated coating is nearly 43 to 1 which is substantially the same as the ratio (40 to 1) of substrate thickness to thickness of the plated coating. It has been found that a ratio of resistivities of substrate to test coating in the range of about 7 to 46 is important for production of accurate results in application of the described sensor for high sensitivity measurements.

Figures 3, 4, 5:
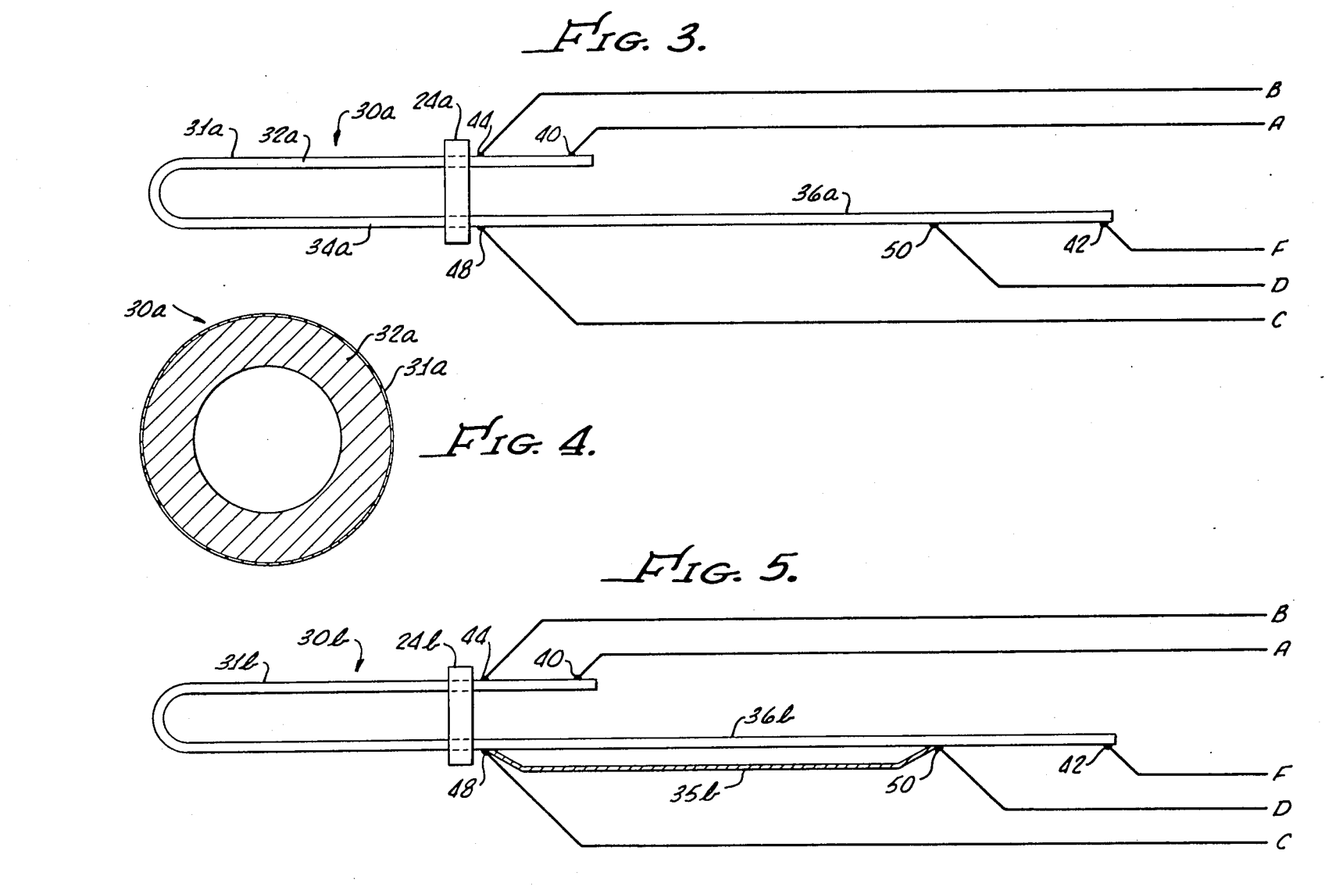
FIG. 3 illustrates the sensor elements of the sensor of FIGS. 1 and 2 wherein both reference and test elements are plated with a thin layer of the metallic element of interest.
FIG. 4 is a cross-section of part of the test element of FIG. 3.
FIG. 5 illustrates a modified sensing element wherein the measuring element is plated with a thin layer of metallic element of interest but the reference element includes a wire.

FIG. 3 illustrates a sensor of the type shown in FIGS. 1 and 2, fabricated in accordance with principles of the present invention. Only a portion of the probe is shown in FIG. 3. A loop 30a, having legs 32a, 34a, extends through apertures in a header disk 24a, being insulated therefrom and sealed thereto by fused glass as previously described. Leg 34a includes an integral reference element portion 36a on the other (inner) side of the header disk and the test and reference elements are connected to terminals A, B, C, D and F by suitable electric leads just as previously described. In this arrangement, the entire sensing element, both test element and reference element, is made of a single loop of tubing just as previously described. However in an exemplary embodiment, the tubing is made of 316 stainless steel having a 4 mil wall thickness and directly upon the tubing is electroplated a coating of copper 31a to a desired test element thickness such as, for example, 0.1 mils. In the fabrication of the sensor illustrated in FIG. 3, the stainless steel tubing substrate is inserted in the holes in disk 24a. Then the fused, hermetic insulation and seal is made by fusing the glass material of the seal at a relatively high temperature. After the sealing and fusion, the entire subassembly is electroplated to the desired thickness with test material 31a of interest, resulting in a cross-section of plated sensor as illustrated in FIG. 4. The entire exterior surface of the test and reference element substrates are plated. It is important that the sealing be performed prior to the electroplating because the high temperature required for fusion of the hermetic seal otherwise may oxidize the plating. Thereafter, the sensor element and disk 24a are mounted in the tubular probe body as shown in FIG. 2 and the periphery of the disk is welded to the probe body. Care is taken in the welding of the disk to the probe body to minimize heat transfer to the plated sensor element because excessive heat could compromise desired qualities of the plated coating. The plated coating does not cover the very small fused glass seal area, which is not electrically conductive, so as to maintain the electrical isolation of the sensing element from the header disk 24a.

Illustrated in FIG. 5 is an alternative configuration of a plated sensor. In this arrangement, a single integral loop of tubing, such as 316 stainless steel tubing, is formed with a test loop portion 30b and an integral reference portion 36b with the legs of the test loop extending through a header disk 24b as previously described. The material of the reference substrate 36b, is the same as the material of the substrate of the test loop 30b.

In this arrangement, only the test loop of portion 30b is electroplated with a coating 31b. Reference element substrate 36b is not coated. In order to provide the reference with the same temperature resistance characteristics as the test element, a reference wire 35b is connected to points 48 and 50 of the reference substrate, at which points the reference resistance measurement leads C and D are connected. The reference wire 35b is made of the same material, such as copper for example, with which the test element 30b is coated and is made of such a diameter as to provide reference wire 35b with a resistance equal to the resistance of the plated coating 31b on the test element substrate. In many applications (particularly in corrosion sensing, where temperature of the monitored fluid may vary widely) it is important that the resistance of the reference element, which varies with temperature, change with variations in temperature in the same manner as does the resistance of the test element. By using the same two materials (e.g., copper and 316 stainless steel) on the reference element as are used on the test element, the net temperature coefficients of resistance of the reference and test elements are made equal to one another.

Where each element, the test element and the reference element, is made of two separate materials, the measurement of resistance of each is effectively the measurement of the resistances of the individual substrate and individual coating, connected in parallel. Thus, a single measurement between terminals B and C is made of the resistance of the test element substrate in parallel with the resistance of the test element coating 31b between these terminals. Similarly, a measurement taken between terminals C and D is a measurement of the resistance of reference element substrate 36b in parallel circuit with resistance of reference wire 35b.

An advantage of the arrangement of FIG. 5 resides in the fact that the probe sensing elements may be assembled to the probe body without fear of damage to the plated coating. The disk 24b may be welded to the probe body, as previously described in connection with the welding of disk 24b to probe body 22, before electroplating the test coating upon the test element substrate. Plating takes place after the header disk is welded to the body. Thus, the reference element may be completely fabricated to include both the electrically conductive substrate 36b and the reference wire 35b, with the header disk 24b being entirely welded to the probe body. Thereafter, the electroplating of the test element substrate to deposit coating 31b may be carried out, thus avoiding detrimental effects on the test element plating of the heat of the welding procedure.

In those situations where the temperature coefficients of resistance of test element substrate and coating are the same, only the test element need be electrically plated with a thin coating upon the electrically conductive substrate, but no coating nor additional reference element comparable to wire 35b in FIG. 5 need be employed with the reference element substrate 35b. In such a situation (e.g., same temperture coefficients of resistance of test substrate and test coating), the position of the point 50 at which terminal D is connected, is simply adjusted to insure that the reference element, which in this case comprises solely an uncoated electrically conductive substrate (such as 316 stainless steel) has the same resistance, at the start of probe life, as the combined parallel resistance of the same substrate (integral with substrate 36b) and its electroplated coating 31b.

Use of materials having widely different thermal coefficients of resistance for corrosion measurement makes it difficult to compensate for changes in temperature. For example, graphite has a negative temperature coefficient of resistance while nearly all metals have positive temperature coefficients of resistance. Thus, the difficulty of compensating for temperature variations and the errors induced by such temperature variations may outweigh any increased sensitivity achieved through the use of graphite as a substrate or part of a substrate. The substrate preferred at present for the practice of this invention is formed of a material that is substantially uniform throughout its thickness, as distinguished from layered or coated substrates which are more difficult and costly to fabricate.

The configurations described above have a number of advantages when employed as sensors in corrosion monitoring. The electroplating process may be employed to fabricate sensors of many desired materials such as copper, silver, zinc, platinum, nickel and like materials which all have relatively low resistivities and all of which can be plated directly upon an electrically conductive substrate of high resistivity such as the 316 stainless steel or other high resistivity electrically conductive substrates.

Sensors fabricated by this process can readily be refurbished by removal of the remainder of the plated coating and replating to the desired thickness, as long as the substrate material has not been damaged. Thus, the probe is readily repairable, particularly where the choice of a substrate is stainless steel. The sensor, at the end of its life, can readily be cleaned by immersion in nitric acid where the plating is silver, copper or nickel or by immersion in a solution of nitric acid and hydrochloric acid where the plating is gold. The stainless steel substrate is resistant to these acid cleaning solutions and thus the refurbishing is a simple matter.

Electroplated coatings on the substrate may be fabricated in any thickness greater than the thickness where resistance of the plated coating is equal to the resistance of the substrate. Coating resistance (which increases as corrosion progresses) should not be more than substrate resistance at the start of corrosion sensor life. This limitation is caused by circuit design constraints and scaling of the instrument employed for measurement of test and reference resistances. If coating resistance is greater than substrate resistance at the start of probe life, the dynamic range of the measuring instrument is decreased. Because of such constraints, the ratio of the test element resistance (the parallel combination of substrate and electroplated coating resistances) to the reference element resistance (parallel combination of substrate and coating resistance), as a practical matter, can range from 1 at the beginning of the life of a sensor to 2 at the end of life. This is for the corrosion sensor, which measures loss of metal due to corrosion or erosion by the environment being monitored. This instrument is constrained for optimum measurement within the range of ratios of test to reference element resistances of from one to two primarily in order to provide high resolution. Other instruments may be made that would permit measurement within other ranges of ratios of test to reference element resistances which ratios may be as much as one to ten. Making an instrument to provide such higher ratio (e.g., up to ten at the end of life) will provide larger measuring ranges but at the cost of resolution which becomes poorer as measuring range increases. Furthermore, resistance of the test element coating must not be significantly less than resistance of the substrate if rapidly degraded measurement resolution is to be avoided.

Typical substrate materials useful in practice of the present invention have electrical resistivities in the range of about 74 microhm-centimeters for the 300 series of stainless steels, and up to 98 microhm-centimeters for nitronic 60, whereas resistivities of typical plating materials to be used for test coatings range from about 1.629 for silver to 10 for platinum and 7.8 for nickel.

In the more important materials that may be employed in practice of the present invention, such as, for example, silver, copper, gold, nickel or platinum plated upon a stainless steel substrate, the range of the ratio of substrate resistivity to test material plating resistivity is in the order of about 7 to 46. Material selected to provide ratios of resistivities in this range therefore will enable ratios of thickness of plated coating to thickness of substrate to also be in the range of about 7 to 46. Sensors of higher sensitivity will employ materials lying in the upper end of this range, as for example, copper electroplated on stainless steel which actually provides a resistivity ratio of about 42.8.

As previously mentioned, thermal coefficients of resistance must be considered in selection of the materials. Such coefficients of various plated materials range from about 0.003 ohms per ohm per degree centigrade to 0.006 ohms per ohm per degree centigrade. Thermal coefficients of resistance of certain substrate materials are lower, but for corrosion monitoring must be reasonably close to the thermal coefficient of resistivity of the plating. For high sensitivity corrosion measurement, it has been found that the ratio of thermal coefficient of resistances of the substrate and plated material should be in the range of about 0.8 to 1.2. In use of the described sensor for monitoring of electrolytic plating as will be discussed below, a considerably wider variation of thermal coefficients of resistance of plated material and substrates is acceptable because dynamic temperature ranges in such plating application are much narrower.

Electroplating

The concepts applied in the manufacture and use of corrosion sensors of the type described above are also applicable to the monitoring of common electroplating processes. Although methods have been developed for the monitoring of electroless plating as shown for example in U.S. Pat. Nos. 4,477,484 and 4,479,980, such electrical resistance method as have been previously known are not capable of use for monitoring of electroplating. It has been found that currents existing in the electrolytic bath, e.g., the plating current, are caused to flow through the sensing element of prior devices and produce noise (to the resistance measurement circuit) of such magnitude as to substantially mask the desired resistance measuring signal. Presently employed methods for monitoring of electrolytic plating include empirical measurements, the use of a test coupon which is removed from the plating bath and weighed. Other arrangements for measuring electrolytic plating also fail to provide a real time or ongoing plating measurement that indicates the thickness of plating as it occurs.

According to another feature of the present invention, the concepts of the sensor described above are readily adapted to continuous, precision, and high sensitivity monitoring of electroplating by an arrangement that substantially eliminates or minimizes the electrolytic bath induced noise in the measuring circuit.

Illustrated in FIG. 6 is a simplified schematic diagram of an electrical resistance sensor of the type described in connection with FIGS. 1 through 4. This sensor is the same as the sensor described above except for the addition of a center tap on the test element and other constraints on ratios of resistivities as will be described below. In this figure, resistor 51 indicates the test resistance, resistor 52 the reference resistance and resistors 54 and 56 portions of the sensor element between the AC excitation terminals A and F and the measurement terminals B and D, respectively. In effect, the circuit is a simple series circuit of the four resistors all connected in end-to-end relation to one another and to the AC excitation terminals A and F. In accordance with a feature of the present invention, the described sensor may be employed for monitoring of electroplating by connecting the sensor in such a fashion as to decrease net noise currents generated in the test element by the electroplating current. To this end, the test element 51 is connected to the plating power supply via a terminal N which is connected to a mid point of the test element 51.

An electrolytic plating operation set up to employ the monitoring sensor described in connection with FIG. 6 is illustrated in FIG. 7. As shown schematically in this figure, an object 58 that is to be plated, is immersed in an electrolytic bath 60 confined in a tank 62 in which is also mounted an anode 64. A DC source of plating voltage 66 has one terminal, such as its negative terminal 68, connected via a lead 70 to the object 58 that is to be plated. The other terminal, the positive terminal 72 of voltage source 66, is connected via a lead 74 to the anode 64. A sensor, generally indicated at 82, constructed substantially as described in connection with FIGS. 1, 2, 3 and 4 is mounted so as to have its loop test element 86 immersed within the bath, preferably at a position close to the object 58. Test element 86, as previously described, may include a loop of thin-walled tubing, a loop of solid wire or a strip loop or a cylindrical test element. Test element 86 is the previously described conductive, high resistivity substrate (such as 316 stainless steel, for example) that may or may not initially have an electroplated coating. To a mid point of this test element 86, that is, to a point electrically equi-distant from the points 44, 48 of the test element at which the resistance measurement is made, namely the points to which terminals B and C are connected (see FIGS. 2, 3, 5, 6, 7), is connected a center tap wire 88. Wire 88 is electrically insulated from the bath except at the very point of its center tap connection to the test element and connected either directly or indirectly, via lead 70, to the plating voltage source 66 negative terminal 68 to which the object 58 is also connected. The sensor 82 includes, as previously described, a plurality of output wires generally indicated at 90, which are connected to the previously described terminals A, B, C, D and F, which in turn are connected to a measuring instrument 94 that will measure and display the thickness of the electroplated coating. An additional terminal (not shown in FIG. 7) may be provided for connection of center tap 88 to the plating power source.

In the absence of the connection of lead 88 to an electrically centered point of test element 86 (e.g., with a plating current lead connected to an end of the test element, for example), current flowing in the electrolytic bath, including the current carrying charged particles involved in the plating process itself, is caused to flow in the test element 86. This current, induced by the bath in the test element throughout the entire area of test element that is exposed to the bath, is significantly greater than the relatively small energizing current for resistance measurement that flows through the test element via the energizing terminals A and F. The current in the bath, which is the plating current that is effective in causing plating of the test element, is unwanted noise in the resistance measuring circuit. Thus, any measurement of voltage between terminals B and C, in the absence of the noise reducing connection to the center tap terminal N, will be greatly affected by the large plating current flowing in the bath. The plating current is so great as to completely override a variation in voltage between terminals B and C that is due only to change in thickness of the test element. However, with the lead 88 connected to the mid point of the test element 86, the plating current in the test element 86 is formed by balanced (equal) components that flow in opposite directions through the test element from the element ends to the center tap 88 and then to the plating power source, thereby cancelling the adverse effect of the plating current upon the resistance measurement. The circuit for the plating current is completed through the power source, from the other terminal 72 of the power source through plating anode 64, and thence through the electrolytic bath 60 itself to the test element 86. Thus, the bath induced current in the test element flows in equal and opposite components to the center tap. The described location of the center tap connection for the plating current has no adverse effect on plating of the test element, but the balanced current components effectively (insofar as resistance measurement is concerned) cancel each other as they flow in opposite directions through the two halves of the test element. Accordingly the resistance of the test element may be readily measured on the basis of the relatively small voltage produced by the exciting source connected to terminals A, F of the sensor.

The center tap performs two functions. First, it connects the sensor in the plating circuit, by connecting the test element to the object to be plated, or directly to the plating power source. Second, it reduces voltage induced in the test element by the plating current sufficiently to enable measurement of test element resistance. Thus, the center tap causes a balanced plating current (balanced as seen by the resistance measuring circuit) to flow in the substrate.

Instead of connecting the center tap to the same power supply used for the plating, it can be connected to a different, separate power source (which is also connected to the plating anode 64, or an equivalent immersed electrode) having equivalent characteristics chosen to ensure the same voltage, current and current density as are afforded by the plating power source.

In a system for electroplating objects, particularly in a system having a large tank in which a number of objects are placed, plating of the objects may vary from place to place in the bath because of differences in current densities and differences in bath characteristics from point to point within the bath. Thus, it is contemplated that one or a plurality of the described sensors, each with its plating current balanced center tap, will be placed at several different points within the bath to provide more detailed real time information of plating progress in different localized areas of the bath.

Figure 8:
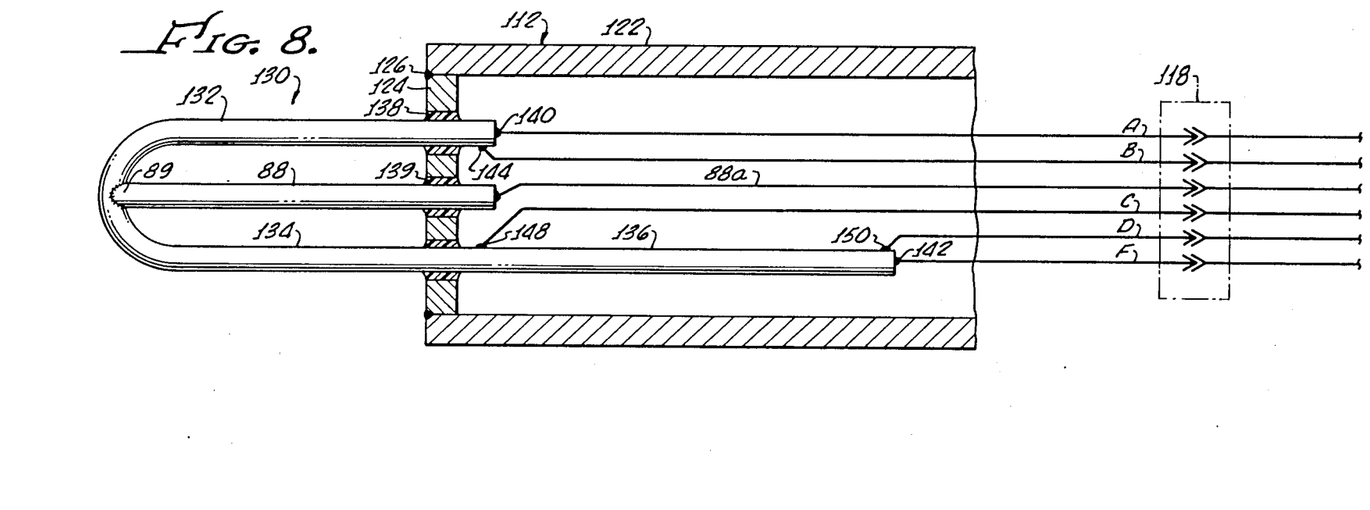
FIG. 8 illustrates a sensor having a noise suppressing connection.

Illustrated in FIG. 8 is an enlarged fragmentary sectional view of the end of the sensor 82 of FIG. 7. This sensor may be identical to the sensor illustrated in FIG. 2 and described above, except for the incision of the noise suppressing lead 88 which conducts plating current between the power source and the test element. Thus, as previously described, tubular test element 130 is mounted in a sensor body 112 being formed of a tubular cylinder 122 having a header disk 124 welded at its periphery 126 to the cylinder 122. A combined reference and test element includes the substantially U-shaped portion 130 having parallel legs 132, 134 with leg 134 extending integrally through the header 124 to form a reference element 136. Header disk 124 is formed with a pair of apertures for reception of test element legs 132, 134, with space between the apertures and the tube legs 132, 134 being filled with a suitable, nonconductive and insulating epoxy. A fused glass sealing material is not required for a plating sensor which is not subject to the intense heat pressure of the corrosive environment in which the corrosion sensor is employed. Therefore, the sealing material may be modified accordingly.

Noise suppressing lead 88 is formed of a relatively large cross-section wire to handle the relatively large plating currents involved and is coated with a suitable insulation such as Teflon except at its end 89 where it is welded to a region that is precisely at the electrical mid-point of the test element 132, 134. The noise suppressing lead extends through a third centrally located aperture in the header disk 124 and is sealed thereto by means of a suitable epoxy 139. The noise suppressing lead 88 is connected via a lead 88a within the interior of cylinder 122 to the connector portion 118, by means of which this lead is connected to the plating voltage source 66 as previously described. The other measuring leads connected to the test and reference elements at points 140, 142, 144, 148 and 150 are connected to the test and reference elements just as previously described for the sensor illustrated in FIG. 2.

It will be readily understood that the center tapped test element sensor of FIG. 8 is merely exemplary of the presently preferred configuration that is described herein. Other sensor configurations may be employed as deemed necessary or desirable.

Figure 9:
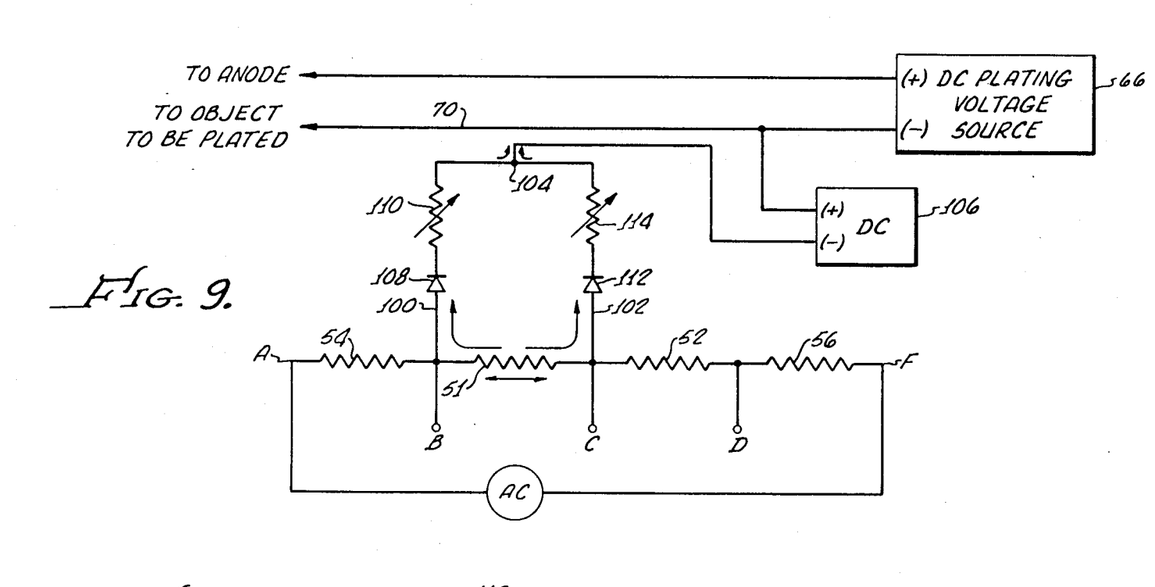
FIG. 9 shows portions of a schematic circuit of a modification of the noise suppressing sensor of FIGS. 6 and 7.

Illustrated in FIG. 9 is a simplified schematic circuit of a modification of the sensor, showing an alternative form of measurement noise suppression. In this schematic circuit, resistors 51, 52, 54 and 56 are exactly as previously described and connected as previously described except for the omission of the center tap lead 88. In place of center tap lead 88 of FIG. 6, the arrangement of FIG. 9 provides first and second noise suppressing leads 100 and 102 connected to respective end points of the test resistor 51 (e.g., to the stainless steel test element substrate). These leads 100, 102 may be connected substantially to the same points on the test element as are the terminals B and C and thus if desired, may be connected to the test element substrate and run inside the sensor body 122.

The two leads 100, 102 are connected together at a common point 104 which in turn is connected either directly to the negative terminal of the DC power plating voltage source 66 just as previously described in connection with the center tap lead 88, or may be connected to such terminal via a small auxiliary voltage boosting source 106 for purposes to be described below. Connected in series in each of the noise suppressing leads 100 and 102, are a diode 108 and a variable resistor 110 for one lead and a diode 112 and a variable resistor 114 for the other lead. Although the leads 100 and 102 are shown connected to the end portions of sensor test resistor 51, they may also be connected to other points of this resistor, such as for example, points equally spaced from the resistor ends and from each other. Preferably, but not necessarily, the connection is such that the leads 100 and 102 are symmetrically connected to the test resistor 51 so as to provide equal and opposite plating current paths through the test resistor 51 and through the two leads 100 and 102. Some unbalance of current components can be adjusted out by the variable resistors.

With connection of the leads 100 and 102 as shown, plating current generated by the bath in the test resistor 51 flows in equal and opposite components through the resistor 51 to its opposite ends and thence in equal current components through each of the leads 100 and 102 to the negative terminal of the power source (assuming for the moment the absence of auxiliary power source 106). Diodes 108 and 112 are inserted in the leads to block the AC energizing current from the measuring source applied via terminals A and F, to insure that the AC measuring current is not shorted out by the leads 100, 102. Variable resistors 110, 114 are inserted in the leads 100, 102 in order to enable precision balancing of the two current components thereby insuring, by adjustment of one or both of the resistors 110 and 114, that the plating current components that flow in opposite directions to the opposite ends of test resistor 51 are indeed precisely equal. Thus, the noise effect on the measurement of the plating current component is precisely eliminated.

Because actual diodes such as diodes 108, 112 have a forward bias or a voltage drop in the order of 0.6 volts in their conducting direction, the use of these diodes in the plating current connection between the resistor 51 and the plating source 66 will result in a smaller plating potential at the measuring resistor (test element) and thus cause the latter to be plated differently than the object that is simultaneously plated in the same bath. To overcome this forward voltage drop across the diodes, the auxiliary potential source 106 is inserted in the common lead between the junction point 104 of the two leads 100, 102 and the main power source 66. The magnitude of the auxiliary power source 106 is chosen so as to make the plating potential at the resistor 51 the same as it would be in the absence of diodes 108, 112 and the resistors 110 and 114. Of course, only one of the adjusting resistors 110, 114 need be used, although a precise adjustment is facilitated by the use of the two adjustable resistors.

The sensor may be of the configuration illustrated in FIGS. 1, 2, 3, 4 or 5, having a test element formed of a thin wall of tube, a wire or flat strip, or a cylinder. The test element and reference element each has an electrically conductive substrate as previously described. For precision measurements with high sensitivity, the substrate resistivity will preferably be significantly higher than the resistivity of the material to be plated. The reference element may be of the type illustrated in FIGS. 3 or 5 and the electrically conductive, high resistivity substrate may be formed of any one of a large number of electrically conductive materials including the stainless steels previously mentioned, other metals, and various types of known electrically conductive plastics. The center tap lead 88 is connected to a mid point of the test element substrate when the sensor is used for monitoring electroplating. The sensor is placed in the bath together with the object to be plated and the anode, and connected as illustrated in FIG. 7. Preferably, before use of the sensor for monitoring electroplating, the substrate will be bare, having no plating or other coating thereon. Thereafter, the electroplating process is commenced (without any need to "sensitize" or conductively coat the substrate) and both the object and test element are plated. As the plating proceeds, measurement of resistance of the test element is accomplished to provide a continuous on-line monitoring of the actual thickness of material plated upon the object.

Although the center tap 88 has been described as especially useful in a sensor for monitoring electroplating, the resistance measurement noise suppression effects of the center tap (and also the arrangement of FIG. 9) are also applicable to the above-described corrosion sensors. Wherever a corrosion sensor is employed to monitor corrosion in an environment in which electrical currents are flowing, the described noise suppressing arrangements will cause such currents as are induced in the substrate by the currents in the environment to flow in balanced, mutually opposing components to effectively cancel the environmentally induced currents insofar as the resistance measurement is concerned. For example, in a cathodic corrosion protection system, the corrosion sensor of any one of the types described above will have induced therein a voltage and current flowing in the test element because of the currents flowing in the environment in which the sensor is immersed. The use of the above-described noise suppressing configurations, employing a sensor of the configuration illustrated in FIGS. 6, 7, 8 and 9, for example, will significantly reduce effects of such induced currents on the resistance meaurement, thus greatly reducing noise in the measurement, at the measurement source. For a corrosion sensor used in a cathodic protection system, having noise suppressing leads as described herein, the ends of the center tap or dual end leads remote from the sensor are connected either to the power source employed in the cathodic protection system or quite simply to the structure (such as the interior of a pipe or other fluid container) that is being protected by the system and which confines the environment being monitored.

In plating monitoring (for reasons similar to those described for corrosion sensing), the ratio of the test element resistance (combined parallel resistance of coating and substrate) to the reference element resistance (combined parallel resistance of substrate and coating, if any) is limited by circuit constraints of the measuring instrument to a range of from 2 at the beginning of life of the sensor to 1 at the end of life. In other words, the sensor may continue to be used for monitoring of the plating until the total parallel resistance of test element substrate and plated coating thereon decreases to a point at which it is equal to the total resistance of the protected reference element. Just as in the case of the corrosion sensor described above, other instruments for measuring the plating sensor resistance may be made to permit an expanded measurement range of up to 10 (at the start of sensor life) to 1 (at the end of life), but at the cost of degraded resolution.

Because the ratio of total test element resistance to total reference element resistance that is acceptable to the measuring instrument may range from 2 at the beginning of sensor life to 1 at the end of sensor life (with a preferred high resolution instrument), it can be shown that the resistance of the plated material may vary from infinite (no plating) to a resistance equal to the substrate material resistance. Resolution degrades rapidly as test element coating resistance becomes less than substrate resistance. Because of the similar geometries of substrate and plating of the test element, that is, equal diameters and equal lengths, the ratio of resistances is same as the ratio of thicknesses of the two materials. Therefore, at the end of life of the sensor, where the resistance of the substrate is the same as the resistance of the test plating, it can be shown that $$\frac{t_p}{t_s} = \frac{\rho_p}{\rho_s}$$

where $t_p$ is thickness of plated material, $t_s$ is thickness of substrate material, $\rho_p$ is resistivity of plated material and $\rho_s$ is resistivity of substrate material.

Therefore, the span of measurement of the sensor for monitoring electroplating is $$S_p = \frac{\rho_p}{\rho_s} t_s$$

where $S_p$ is the span of life of the plating measurement in mils. From this equation for $S_p$ it will be seen that one can have a very small plating measurement span ($S_p$) with an exceedingly high resolution when using materials with large ratios of resistivities and even when using relatively thick ($t_s$) substrates. Such an arrangement is particularly useful when electroplating precious metals such as gold, silver and platinum. This is true both because of the economics involved and because the plating of these elements is generally exceedingly thin and to close tolerances.

In other applications, where a larger plating measurement life span is required, a lower ratio of resistivities would be desirable. In such a situation, a desired larger life span, the sensor substrate may be copper and material to be plated on the object and upon the substrate could be copper or silver. Thus, it will be seen from the life span equation above, and from constraints of the measurement circuitry which constrain a measurement to the above-described range of resistance ratios of 2 to 1, that the thickness of the substrate is a function of the measurement span required and resistivity of the substrate.

The above-described plating monitor sensor, having a center tap on the test element substrate as previously described (and also the sensor of FIG. 9), may employ many other physical configurations in addition to those described in connection with the description of the corrosion probe. For use in plating monitoring, the sensor may take any suitable configuration such as a configuration substantially similar to that of the object being plated. For example, in circuit board plating, the sensor test element may be in the form of a test coupon similar in configuration to the circuit board substrate that is to be plated. The test coupon may be of a non-conductive material that is coated in any suitable manner, as for example with an initial coating of electroless plating to cause it to be conductive, and the noise suppressing leads will be connected as previously described. Although suitable acceptable measurements of corrosion may be made in some environments with the described sensor without the center tap, it is essential that the center tap (or other noise suppressing leads) be employed in making the resistance measurement for monitoring of electrolytic plating in order to eliminate effects of the plating current upon the resistance measurement. For example, in monitoring through-hole plating of a circuit board, a test coupon is made of dielectric material having a number of holes therein in an arrangement and configuration similar to the dielectric object being plated (also having an initial thin electroless conductive coating). The test coupon is initially coated as by electroless plating or other suitable method, to provide an electrically conductive test coupon substrate having a continuous electrical path along the substrate surface from one hole to another an including the walls of the holes. The center tap is connected to an electrical midpoint of the test coupon or a pair of noise suppressing leads is connected to the ends of the test coupon, as previously described, and the apertured test coupon may be employed as a sensor for monitoring plating of through-hole circuit boards in the manner described above.

With a life span, as measured in mils, that is greater than the thickness of desired plating, the same probe can be used for many successive plating operations. For example, if the life span of the probe is 0.329 mils and a plating thickness of 0.03 mils is desired, the same probe can be used ten successive times (without refurbishing) to monitor ten successive 0.03 mil plating operations. For each successive 0.03 mil plating operation the sensor starts with the plated test element coating of a thickness acquired in the previous 0.03 mil plating. In the example chosen, plating of 0.329 mils of gold (acquired after the tenth plating operation) would have the same resistance as a 10 mil thickness of 316 stainless steel. Therefore, at the end of the sensor life (e.g., when sensor plating thickness is 0.329 mils) the two parallel resistance (plating and substrate) are equal. This life span of 0.329 mils in plating gold upon stainless steel allows plating to continue or to be repeated until the thickness of the plating on the stainless steel test element substrate is such that the resistance of the gold plating is equal to the resistance of the substrate. As previously mentioned, constraints of the measuring instrument make it impractical to measure test element resistance if it is significantly less than the reference resistance.

Among the pairs of materials, test element and substrate respectively, that will be most commonly employed are nickel, gold and copper plated on 316 stainless steel; silver or copper on copper; rhodium on 316 stainless steel; and nickel on carbon steel. As previously stated, a variation of thermal coefficients of resistivity of the plating and substrate respectively outside of the range of 0.8 to 1.2 for the ratio of thermal coefficients of resistance can be accepted for plating monitoring because of the relatively small temperature ranges encountered.

As in the corrosion sensor, the sensor employed in plating monitoring may be readily reused by stripping the plating material from the substrate, particularly where the substrate is stainless steel which is insensitive to the cleaning agents employed.

There have been described methods and apparatus for high sensitivity monitoring of corrosion and/or electroplating employing relatively thick, structurally self-sufficient and self-supporting electrically conductive substrates of high resistivity, having measurement coatings electroplated thereon and with the coatings varying between thicknesses relative to substrate thickness at the beginning of life in specified ranges. Ratios of resistivities of the substrate to the plated coating are high, in the range of about 7 to 46. Less constraints of resistivity ratios and differences in thermal coefficients of resistance are imposed upon the sensor when used in plating monitoring ad especially in the latter application, provision is made for minimizing noise currents induced in the exposed sensing element by the currents flowing in the electrolytic bath.

The foregoing detailed description is to be clearly understood as given by way of illustration and example only, the spirit and scope of this invention being limited soley by the appended claims.

What is claimed is:

1. A corrosion monitoring probe including an electrical resistance sensor, said sensor comprising:
   a test element adapted to be exposed to an environment in which monitoring is to be accomplished,
   a reference element protected from such environment, and
   means for comparing electrical resistances of said elements for determination of test element thickness,
   said test element comprising a substrate formed of electrically conductive material having a relatively high electrical resistivity, and an electrically conductive test coating on said substrate, said test coating having an electrical resistivity considerably less than said substrate resistivity, wherein the ratio of substrate thickness to test coating thickness at the start of probe life is approximately the same as the ratio of substrate resistivity to coating resistivity.

2. A sensor for monitoring electroplating of an object immersed in an electrolytic bath with an electrode, said object and electrode being connected in a plating circuit having a plating power source, said sensor comprising:
   an electrically conductive substrate adapted to be immersed in said bath and to be plated as said object is plated, said substrate being subject to plating current caused to flow therein by said electrolytic bath,
   means for measuring electrical resistance of said substrate, said means for measuring being adversely affected by plating current flowing in said substrate, and
   means for reducing adverse effects of said plating current on said means for measuring, said means for reducing adverse effects of said plating current comprising unidirectional conducting means for coupling opposite ends of said substrate to each other and to said power source.

3. A method of monitoring corrosion of a fluid environment comprising the steps of mounting an electrically conductive substrate and an electrically conductive reference element in a sensor body with said reference element protected from an environment in which said sensor is to be immersed and with said substrate positioned for exposure to such environment, electroplating a conductive test coating on said substrate, said substrate having a greater resistivity and a greater thickness than said test coating, said step of electroplating comprising plating said test coating upon said substrate to a thickness at which the resistance of the test coating is about equal to the resistance of said substrate, exposing said test coating to said environment to cause corrosion of said test coating and decrease of its thickness to a thickness at which the resistance of the test coating is greater than the resistance of said substrate, and comparing the combined resistance of said substrate and test coating with the resistance of said reference element.

4. The method of claim 3 wherein said step of mounting comprises the steps of positioning the substrate to extend through an apertured header, and sealing and electrically insulating said substrate to said header with a fused sealant before said step of electroplating.

5. The method of claim 3 including the step of connecting a reference conductor in parallel with said reference element, said reference conductor having the same resistance as said first mentioned resistance of said test coating.

6. An electrical resistance sensor comprising:
a substrate formed of electrically conductive substrate material having a substrate resistivity and having a substrate thickness sufficient to enable said sensor to be self-supporting,
an electrically conductive test material electroplated on the substrate, said test material having a resistivity substantially less than said substrate resistivity and a thickness substantially less than said substrate thickness, and
a center tap on said substrate connected to a point of fixed potential.

7. An electrical resistance sensor comprising:
a test element adapted to be exposed to an environment in which monitoring is to be accomplished,
a reference element protected from such environment, and
means for comparing electrical resistances of said elements for determination of test element thickness,
said test element comprising a substrate formed of electrically conductive material having a relatively high electrical resistivity, and an electrically conductive test coating on said substrate, said test coating having an electrical resistivity considerably less than said substrate resistivity,
said environment inducing electrical current in said substrate that adversely affects said means for comparing electrical resistance, and means connected with said substrate for reducing adverse effects of said electrical current,
said means connected with said substrate comprising means for connecting said substrate to cause electrical current induced by said environment in said substrate to flow in oppositely directed components in said substrate.

8. An electrical resistance sensor comprising:
a test element adapted to be exposed to an environment in which monitoring is to be accomplished,
a reference element protected from such environment, and
means for comparing electrical resistances of said elements for determination of test element thickness,
said test element comprising a substrate formed of electrically conductive material having a relatively high electrical resistivity, and an electrically conductive test coating on said substrate, said test coating having an electrical resistivity considerably less than said substrate resistivity,
said environment inducing electrical current in said substrate that adversely affects said means for comparing electrical resistance, and means connected with said substrate for reducing adverse effects of said electrical current,
said means for reducing adverse effects of said electrical current comprising a center tap on said substrate connected to a point of fixed potential.

9. A method of monitoring electrolytic plating comprising
immersing an electrode and an object to be plated in an electrolytic bath,
making a plating connection between a plating power source and the object and electrode to cause plating current to flow in the object,
immersing an electrically conductive test element in the electrolytic bath,
making a monitor connection between the plating power source and the test element to cause plating current to flow in the test element,
measuring resistance of said test element,
the plating current in the test element tending to cause adverse effects on the measuring of resistance, and
making the monitor connection at a selected region of the test element so as to reduce said adverse effects by causing the plating current to flow in oppositely directed components in the test element.

10. The method of claim 9 including the step of causing plating current to flow in the test element in substantially equal and opposite components by making the monitor connection to a central region of the test element.

11. The method of claim 9 including the step of causing the plating current to flow in the test element in substantially equal and opposite components by making the monitor connection between the plating power source and first and second mutually spaced regions on said test element.

12. An electrical resistance sensor comprising:
a test element adapted to be exposed to an environment in which monitoring is to be accomplished,
a reference element protected from such environment,
means for comparing electrical resistances of said elements for determination of test element thickness,
said test element comprising a substrate formed of electrically conductive material having a relatively high electrical resistivity, and an electrically conductive test coating on said substrate, said test coating having an electrical resistivity considerably less than said substrate resistivity, and a noise suppressing lead connected to said test element,
said noise suppressing lead comprising a center tap on said test element.

13. An electrical resistance sensor comprising:
a test element adapted to be exposed to an environment in which monitoring is to be accomplished,
a reference element protected from such environment, means for comparing electrical resistances of said elements for determination of test element thickness,
said test element comprising a substrate formed of electrically conductive material having a relatively high electrical resistivity, and an electrically conductive test coating on said substrate, said test coating having an electrical resistivity considerably less than said substrate resistivity, and a noise suppressing lead connected to said test element,
said noise suppressing lead comprising first and second unidirectional conductive means connected to opposite ends of said test element.

14. An electrical resistance sensor comprising:
a substrate formed of electrically conductive substrate material having a substrate resistivity and having a substrate thickness sufficient to enable said sensor to be self-supporting,
an electrically conductive test material electroplated directly on the substrate, said test material having a resistivity substantially less than said substrate resistivity and a thickness substantially less than said substrate thickness, and
a noise suppressing lead connected to said test element, said noise suppressing lead comprising a center tap on said test element.

15. An electrical resistance sensor comprising:
a substrate formed of electrically conductive substrate material having a substrate resistivity and having a substrate thickness sufficient to enable said sensor to be self-supporting,
an electrically conductive test material electroplated directed on the substrate, said test material having a resistivity substantially less than said substrate resistivity and a thickness substantially less than said substrate thickness, and
a noise suppressing lead connected to said test element, said noise suppressing lead comprising first and second unidirectional conductive means connected to opposite ends of said test element.

16. The method of monitoring corrosion of a fluid environment comprising the steps of:
mounting an electrically conductive substrate and an electrically conductive reference element in a sensor body with said reference element protected from an environment in which said sensor is to be immersed and with said substrate positioned for exposure to such environment,
electroplating a conductive test coating on said substrate, said substrate having a greater resistivity and a greater thickness than said test coating,
said step of electroplating comprising plating said test coating upon said substrate to a thickness at which the resistance of the test coating is about equal to the resistance of said substrate,
exposing said test coating to said environment to cause corrosion of said test coating and decrease of its thickness to a thickness at which the resistance of the test coating is greater than the resistance of said substrate,
comparing the combined resistance of said substrate and test coating with the resistance of said reference element, and
connecting a center tap between said substrate and a point of fixed potential.

17. The method of monitoring corrosion of a fluid environment comprising the steps of:
mounting an electrically conductive substrate and an electrically conductive reference element in a sensor body with said reference element protected from an environment in which said sensor is to be immersed and with said substrate positioned for exposure to such environment,
electroplating a conductive test coating on said substrate, said substrate having a greater resistivity and a greater thickness than said test coating,
said step of electroplating comprising plating said test coating upon said substrate to a thickness at which the resistance of the test coating is about equal to the resistance of said substrate,
exposing said test coating to said environment to cause corrosion of said test coating and decrease of its thickness to a thickness at which the resistance of the test coating is greater than the resistance of said substrate,
comparing the combined resistance of said substrate and test coating with the resistance of said reference element, and
forming first and second unidirectional conductive paths between opposite ends of said substrate and a point of fixed potential.

18. An electrical resistance sensor comprising:
a test element adapted to be exposed to an environment in which monitoring is to be accomplished and in which electrical currents are flowing,
a reference element protected from such environment, means for comparing electrical resistances of said elements for determination of test element thickness,
noise suppressing means connected to said test element for reducing adverse effects of said electrical currents on said means.for comparing,
said noise suppressing means comprising a center tap connected to said test element.

19. An electrical resistance sensor comprising:
a test element adapted to be exposed to an environment in which monitoring is to be accomplished and in which electrical currents are flowing,
a reference element protected from such environment,
means for comparing electrical resistances of said elements for determination of test element thickness,
noise suppressing means connected to said test element for reducing adverse effects of said electrical currents on said means for comparing,
said noise suppressing means comprising unidirectional conducting means connected to opposite ends of said test element.

20. In combination with a vessel that confines a fluid in which electrical currents flow, an electrical resistance sensor comprising:
a test element immersed in said fluid and being subject to noise currents induced therein by said electrical currents which flow in said fluid, means for measuring electrical resistance of said test element, and noise suppressing means connected between said test element and a point of fixed potential for causing components of noise currents therein to flow in mutually opposite directions in said test element, thereby reducing adverse effects of said electrical currents upon said means for measuring.

21. In combination with a vessel that confines a fluid in which electrical currents flow, and electrical resistance sensor comprising:

a test element immersed in said fluid, means for measuring electrical resistance of said test element, and noise suppressing means connected between said test element and a point of fixed potential for reducing adverse effects of said electrical currents upon said means for measuring, said noise suppressing means comprising a center tap on said test element.

22. In combination with a vessel that confines a fluid of which corrosive tendencies are to be monitored, an electrical resistance corrosion sensor comprising:

a test element immersed in said fluid, means for measuring electrical resistance of said test element, said fluid having electric current flowing therein that tends to adversely effect said means for measuring, and means for reducing adverse effects of said electric current on said means for measuring comprising means for providing an electrically conductive path between a point intermediate the ends of said test element and said vessel.

23. In combination with a vessel that confines a fluid of which corrosive tendencies are to be monitored, an electrical resistance corrosion sensor comprising:

a test element immersed in said fluid, means for measuring electrical resistance of said test element, said fluid having electric current flowing therein that tends to adversely effect said means for measuring, means for reducing adverse effects of said electric current on said means for measuring comprising means for providing an electrically conductive path between said test element and said vessel, said means for providing an electrically conductive path comprising a center tap on said test element.

24. An electrical resistance sensor comprising:

electrically conductive test and reference elements connected in series to one another, said test element adapted to be exposed to an environment in which a measurement is to be made, said environment having current flowing therein that tends to generate noise current in the test element exposed to such environment, means for applying an excitation potential to said elements, measurement leads connected to said elements for measuring resistance of said test and reference elements, and noise suppressing means connected to said test element for causing noise current components to flow in mutually opposite directions in said test element, thereby decreasing net noise current in said test element.

25. An electrical resistance sensor comprising:

electrically conductive test and reference elements connected in series to one another, said test element adapted to be exposed to an environment in which a measurement is to be made, said environment having current flowing therein that tends to generate noise current in the test element exposed to such environment, means for applying an excitation potential to said elements, measurement leads connected to said elements for measuring resistance of said test and reference elements, and noise suppressing means connected to said test element for decreasing net noise current in said test element, said noise suppressing means comprising a center tap on said test element adapted to be connected to a point of fixed potential.

26. An electrical resistance sensor comprising:

a test element adapted to be exposed to an environment in which monitoring is to be accomplished, a reference element protected from such environment, and means for comparing electrical resistances of said elements for determination of test element thickness, said test element comprising a substrate formed of electrically conductive material having a relatively high electrical resistivity, and an electrically conductive test coating on said substrate, said test coating having an electrical resistivity considerably less than said substrate resistivity, said environment inducing electrical current in said substrate that adversely affects said means for comparing electrical resistance, and means connected with said substrate for reducing adverse effects of said electrical current, said substrate being a self-supporting, highstrength material that is substantially uniform throughout its thickness and having an exterior surface, said test coating being electroplated directly on said material over all of said exterior surface, said means connected with said substrate comprising means for connecting said substrate to cause electrical current induced by said environment in said substrate to flow in oppositely directed components in said substrate.

27. An electrical resistance sensor comprising:

a test element adapted to be exposed to an environment in which monitoring is to be accomplished, a reference element protected from such environment, and means for comparing electrical resistances of said elements for determination of test element thickness, said test element comprising a substrate formed of electrically conductive material having a relatively high electrical resistivity, and an electrically conductive test coating on said substrate, said test coating having an electrical resistivity considerably less than said substrate resistivity, said environment inducing electrical current in said substrate that adversely affects said means for comparing electrical resistance, and means connected with said substrate for reducing adverse effects of said electrical current, said substrate being a self-supporting, high-strength material that is substantially uniform throughout its thickness and having an exterior surface, said test coating being electroplated directly on said material over all of said exterior surface, said means for reducing adverse effects of said electrical current comprising a center tap on said substrate connected to a point of fixed potential.

28. A resistance probe for use in monitoring electrolytic plating of an object immersed in an electrolytic bath and connected to a plating power source, said probe comprising:

an electrically conductive test element adapted to be immersed in the electrolytic bath with the object to be plated, means for electrically connecting resistance measuring apparatus to first and second points on said test element, and means for electrically connecting the plating power source to said test element between said first and second points.

29. An electrical resistance sensor comprising a test element adapted to be exposed to an environment in which monitoring is the be accomplished and in which electrical currents are flowing, a reference element protected from such environment, means for comparing electrical resistances of said elements for determination of test element thickness, and noise suppressing means connected to said test element for reducing adverse effects of said electrical currents on said means for comparing, wherein said means for comparing includes measuring means connected to first and second points of said test element, and wherein said noise suppressing means includes means connected to said test element at a point between said first and second points.

30. An electrical resistance sensor comprising:

a test element adapted to be exposed to an environment in which monitoring is to be accomplished, a reference element protected from such environment, and means for comparing electrical resistance of said elements for determination of test element thickness, said test element comprising a substrate formed of electrically conductive material having a relatively high electrical resistivity and a relatively large cross sectional area, and an electrically conductive test coating on said substrate, said test coating having an electrical resistivity and cross sectional area considerably less than said substrate resistivity and cross sectional area, wherein said test element substrate is formed substantially entirely of said material.

31. An electrical resistance sensor comprising:

a substrate formed of electrically conductive substrate material having a substrate resistivity and having a substrate thickness sufficient to enable said sensor to be self-supporting, an electrically conductive test material electroplated on the substrate, said test material having a resistivity substantially less than said substrate resistivity and a thickness substantially less than said substrate thickness, the ratio of substrate resistivity to test material resistivity being in the range of about seven to forty-six.

32. An electrical resistance sensor comprising:

a substrate formed of electrically conductive substrate material having a substrate resistivity and having a substrate thickness sufficient to enable said sensor to be self-supporting, an electrically conductive test material electroplated on the substrate, said test material having a resistivity substantially less than said substrate resistivity and a thickness substantially less than said substrate thickness, each of (a) the ratio of substrate resistivity to test material resistivity and (b) the ratio of substrate thickness to test coating thickness before the sensor has been used, being about forty to one.

* * * * *

UNITED STATES PATENT AND TRADEMARK OFFICE
CERTIFICATE OF CORRECTION

PATENT NO. : 4,755,744

DATED : July 5, 1988

INVENTOR(S) : CLIFFORD G. MOORE, ET AL

It is certified that error appears in the above-identified patent and that said Letters Patent is hereby corrected as shown below:

On page 1 of the patent, section [21], The Appln. No. shown is incorrect. 21,013 should be deleted, and ---821,013--- inserted.

Signed and Sealed this

Thirty-first Day of January, 1989

Attest:

DONALD J. QUIGG

Attesting Officer

Commissioner of Patents and Trademarks